US009650649B2

United States Patent
Laer et al.

(10) Patent No.: US 9,650,649 B2
(45) Date of Patent: May 16, 2017

(54) LCMV-GP-VSV-PSEUDOTYPED VECTORS AND TUMOR-INFILTRATING VIRUS-PRODUCING CELLS FOR THE THERAPY OF TUMORS

(75) Inventors: Dorothee Von Laer, Innsbruck (AT); Tsanan Heimann, Mainz (DE)

(73) Assignee: VIRATHERAPEUTICS GMBH, Innsbruck (AT)

(*) Notice: Subject to any disclaimer, the term of this patent is extended or adjusted under 35 U.S.C. 154(b) by 119 days.

(21) Appl. No.: 13/123,175

(22) PCT Filed: Oct. 8, 2009

(86) PCT No.: PCT/EP2009/007230
§ 371 (c)(1),
(2), (4) Date: Jun. 29, 2011

(87) PCT Pub. No.: WO2010/040526
PCT Pub. Date: Apr. 15, 2010

(65) Prior Publication Data
US 2011/0250188 A1 Oct. 13, 2011

(30) Foreign Application Priority Data
Oct. 8, 2008 (DE) .................. 10 2008 050 860

(51) Int. Cl.
*A01N 63/00* (2006.01)
*C12N 15/86* (2006.01)
*C12N 13/00* (2006.01)
*A61K 48/00* (2006.01)

(52) U.S. Cl.
CPC .... *C12N 15/86* (2013.01); *C12N 2760/10122* (2013.01); *C12N 2760/20243* (2013.01); *C12N 2760/20245* (2013.01); *C12N 2810/6072* (2013.01)

(58) Field of Classification Search
CPC ................. C12N 9/1211; C12N 15/86; C12Y 207/01021; A61K 38/45; A61K 35/766
USPC ....................................... 424/93.2
See application file for complete search history.

(56) References Cited

U.S. PATENT DOCUMENTS

2007/0059291 A1* 3/2007 McCray, Jr. ......... C07K 14/005
424/93.2

FOREIGN PATENT DOCUMENTS

| EP | 1006196 B1 | 11/1999 |
| WO | 03005964 A2 | 1/2003 |
| WO | WO 03/005964 * | 1/2003 |
| WO | 2006008074 A1 | 1/2006 |
| WO | WO 2006/008074 A1 * | 1/2006 |

OTHER PUBLICATIONS

Lee et al, 2006, Vaccine 24:2928-2934.*
Bruns et al., 1984, Virology 137:49-57.*
Schnell et al 1996, Proc. Natl. Acad. Sci. (USA) 93:11359-11365.*
Lichty et al 2004, Trends in Mol. Med. 10:210-216.*
Bergman et al 2007, Int. J. Cancer. 121:425-430.*
Barber et al 2004, Viral Immunol. 17: 516-527.*
Ahmed et al., "Immune Response in the Absence of Neurovirulence in Mice Infected with M Protein Mutant Vesicular Stomatitis Virus", Journal of Virology: 82(18): pp. 9273-9277 (Sep. 2008).
Barber, "Vesicular Stomatitis Virus as an Oncolytic Vector", Viral Immunol, 17(4): pp. 516-527 (2004).
Beyer et al., "Oncoretrovirus and Lentivirus Vectors Pseudotyped with Lymphocytic Choriomeningitis Virus Glycoprotein: Generation, Concentration, and Broad Host Range", Journal of Virology, 76(3): pp. 516-527 (Feb. 2002).
Carlsson et al., "Liquid-Overlay Culture of Celular Spheroids", Recent Results Cancer Research, 95: pp. 1-23 (1984).
Culver et al., "In Vivo Gene Transfer with Retroviral Vector-Producer Cells for Treatment of Experimental Brain Tumors", Science, 256(5063): pp. 1550-1552 (Jun. 12, 1992).
Cutter et al., "Gene Therapeutics: the Future of Brain Tumor Therapy?", Expert Review of Anticancer Therapy, 6 (7): pp. 1053-1034 (2006).
Dai et al., "Glioma Models", Biochim Biophys Acta., 1551(1): pp. M19-M27 (Aug. 31, 2001).
Desforges et al., "Different Host-Cell Shutoff Strategies Related to the Matrix Protein Lead to Persistence of Vesicular Stomatitis Virus Mutants on Fibroblast Cells", Virus Res., 76(1): pp. 87-102 (Jul. 2001).
Finke et al., "Recombinant Rhabdoviruses: Vectors for Vaccine Development and Gene Therapy", Curr Top Microbiol Immunol, 292: pp. 165-200 (2005).
Fischer et al., "A Retroviral Packaging Cell Line for Pseudotype Vectors Based on Glioma-Infiltrating Progenitor Cells", Journal of Gene Medicine, 9: pp. 335-344 (2007).
Fukuhara et al., "Oncolytic Herpes Simplex Virus Vector G47? in Combination with Androgen Ablation for the Treatment of Human Prostate Adenocarcinoma", Clin Cancer Res., 11(21): pp. 7886-7890 (Nov. 1, 2005).
Garbutt et al., "Properties of Replication-Competent Vesicular Stomatitis Virus Vectors Expressing Glycoproteins of Filoviruses and Arenaviruses," J Virol., 78(10): pp. 5458-5465 (May 2004).

(Continued)

*Primary Examiner* — Scott Long
*Assistant Examiner* — Kelaginamane T Hiriyanna
(74) *Attorney, Agent, or Firm* — Faegre Baker Daniels LLP (57) ABSTRACT

The invention relates to recombinant VSV viruses and viral vectors which produce a glycoprotein GP of the lymphocyte choriomeningitis virus (LCMV) instead of the G protein of the VSV, to virus producing cells which produce LCMV-GP-pseudotyped VSV virions, and to the use of said vectors and cells in the therapy of solid tumors, especially brain tumors.

11 Claims, 3 Drawing Sheets

(56) References Cited

OTHER PUBLICATIONS

Ge et al., "Generating Vesicular Stomatitis Virus Pseudotype Bearing the Severe Acute Respiratory Syndrome Coronavirus Spike Envelope Glycoprotein for Rapid and Safe Neutralization Test or Cell-Entry Assay", Ann N Y Acad Sci., 1081: pp. 246-248 (2006).
Haller et al., "The Interferon Response Circuit: Induction and Suppression by Pathogenic Viruses", Virology, 344 (1): pp. 119-130, (Jan. 5, 2006).
Hanika et al., "Use of Influenza C Virus Glycoprotein HEF for Generation of Vesicular Stomatitis Virus Pseudotypes", J Gen Virol., 86(Pt 5): pp. 1455-1465 (May 2005).
Holland et al., "Gliomagenesis: Genetic Alterations and Mouse Models", Nat Rev Genet., ;2(2): pp. 120-129 (Feb. 2001).
Irie et al., "Modifications of the PSAP Region of the Matrix Protein Lead to Attenuation of Vesicular Stomatitis Virus in Vitro and in Vivo", J Gen Virol., 88 (Pt 9): pp. 2559-2567 (Sep. 2007).
Janzen et al., "A Monomeric GTPase-Negative MxA Mutant with Antiviral Activity", J Virol, 74(17): pp. 8202-8206, (Sep. 2000).
Jayakar et al., "Identification of Two Additional Translation Products from the Matrix (M) Gene that Contribute to Vesicular Stomatitis Virus Cytopathology", J Virol., 76(16): pp. 8011-8018, (Aug. 2002).
Jiang et al, "Pluripotency of Mesenchymal Stem Cells Derived from Adult Marrow", Nature 418: pp. 41-49 (2000).
Kikuchi et al., "Antitumor Activity of Interleukin 12 Against Interleukin 2-Transduced Mouse Glioma Cells" Cancer Lett, 135: pp. 47-51 (1999).
Loew et al., "Retroviral Vectors Containing Tet-Controlled Bidirectional Transcription Units for Simultaneous Regulation of Two Gene Activities", JMol GenMed, 2(1): pp. 107-118 (2006).
Lun et al., "Effects of Intravenously Administered Recombinant Vesicular Stomatitis Virus (VSV ? M51) on multifocal and Invasive Gliomas", J Natl Cancer Inst., 98(21): pp. 1546-1557 (Nov. 1, 2006).
Majewski et al., "Interleukin-12 Inhibits Angiogenesis Induced by Human Tumor Cells in Vivo", J. Invest. Dermatol., 106: pp. 1114-1118(1996).
Miletic et al., "Retroviral Vectors Pseudotyped with Lymphocytic Choriomeningitis Virus", J. Virol., 73: pp. 6114-6116 (1999).
Miletic et al., "Selective Transduction of Malignant Glioma by Lentiviral Vectors Pseudotyped with Lymphocytic Choriomeningitis Virus Glycoproteins", Hum Gene Ther., 15: pp. 1091-1100 (Nov. 2004).
Miletic et al., "Normal Brain Cells Contribute to the Bystander Effect in Suicide Gene Therapy of Malignant Glioma", Clin Cancer Res, 13(22): pp. 6761-6768 (Nov. 15, 2007).
Miletic et al., "Bystander Killing of Malignant Glioma by Bone Marrow-Derived Tumor Infiltrating Progenitor Cells Expressing a Suicide Gene" Molecular Therapy 15(7): pp. 1373-1381 (Jul. 2007).
Owens et al., "Cytoplasmic Domain Requirement for Incorporation of a Foreign Envelope Protein into Vesicular Stomatitis Virus" J Virol. 67(1): pp. 360-365 (Jan. 1993).
Pavlovic et al., "Human and Mouse Mx Proteins Inhibit Different Steps of the Influenza Virus Multiplication Cycle" J Virol., 66(4): pp. 2564-2569 (Apr. 1992).
International Search Report for PCT/EP2009/007230, issued on Mar. 4, 2010.
Written Opinion for PCT/EP2009/007230, issued on Mar. 4, 2010.
Sakariassen et al., "Angiogenesis-Independent Tumor Growth Mediated by Stem-Like Cancer Cells" Proc Natl Acad Sci U S A, 103(44): pp. 16466-16471 (Oct. 31, 2006).
Shinosaki et al., "Prophylactic alpha interferon treatment increases the therapeutic index of oncolytic vesicular stomatitis virus virotherapy for edvanced hepatocellular carcinoma in immune-competent rats", J Virol., 79(21): pp. 13705-13713.
Shir et al., "Gene Therapy for Glioblastoma: Future Perspective for Delivery Systems and Molecular Targets", Cell Mol Neubiol, 21(6): pp. 645-656, (Dec. 2001).

Short et al., Gene delivery to glioma cells in rat brain by grafting of a retrovirus packaging cell line. J Neurosci Res. 27(3): pp. 427-439 (Nov. 1990).
Spann et al., "Genetic Recombination During Coinfection of Two Mutants of Human Respiratory Syncytial Virus" J Virol., 77(20): pp. 11201-11211 (Oct. 2003).
Staeheli et al., "Inhibition of Vesicular Stomatitis Virus mRNA Synthesis by Human MxA Protein", J Virol. 65(8): pp. 4498-4501 (Aug. 1991).
Sumia et al., Inflammatory and Anti-glioma Effects of an Adenovirus Expressing Human Soluble Fms-like Tyrosine Kinase 3 Ligand (hsFlt3L): Treatment with hsFlt3L Inhibits Intracranial Glioma Progression. Molecular Therapy 10(6): pp. 1071-1084 (Dec. 2004).
Tani et al., "Replication-Competent Recombinant Vesicular Stomatitis Virus Encoding Hepatitis C Virus Envelope Proteins", J Virol., 81(16): pp. 8601-8612, (Aug. 2007) (Epub Jun. 6, 2007).
Toda et al., "In Situ Cancer Vaccination: An IL-12 Defective Vector/Replication-Competent Herpes Simplex Virus Combination Induces Local and Systemic Antitumor Activity", J. Immunol. 160: pp. 4457-4464 (1998).
Trajcevski et al., "Characterization of a semi-replicative gene delivery system allowing propagation of complementary defective retroviral vectors", J Gene Med., 7(3): pp, 276-87 (Mar. 2005).
Tyminski et al., "Brain Tumor Oncolysis with Replication-Conditional Herpes Simplex Virus Type 1 Expressing the Prodrug-Activating Genes, CYP2B1 and Secreted Human Intestinal Carboxylesterase , in Combination with Cyclophosphamide and Irinotecan", Cancer Res., 65(15): pp. 6850-6857 (Aug. 1, 2005).
Wollman et al., "Variable Deficiencies in the Interferon Response Enhance Susceptibility to Vesicular Stomatitis Virus Oncolytic Actions in Glioblastoma Cells but not in Normal Human Glial Cells", J Virol., 81(3): pp. 1479-1491 (Feb. 2007).
Zimmer et al., "Cleavage at the Furin Consensus Sequence RAR/KR109 and Presence of the Intervening Peptide of the Respiratory Syncytial Virus Fusion Protein Are Dispensable for Virus Replication in Cell Culture, "J Virol., 76(18): pp. 9218-9224, (Sep. 2002).
Beyer et al., "Recombinant Expression of Lymphocytic Chroriomeningitis Virus Strain WE Glycoproteins: a Single Amino Acid Makes the Difference" XP-002347069; Journal of Virology, Jan. 2001; vol. 75, No. 2; p. 1061-1064.
European Search Report for Application No. 13153949.6-1410; dated Apr. 29, 2013; 6 pgs.
Muik, et al., "Pseudotyping Vesicular Stomatitis Virus with Lymphocytic Choriomenengitis Virus Glycoproteins Enhances Infectivity for Glioma Cells and Minimizes Neurotropism" Journal of Virology, Jun. 2011, vol. 85, No. 11, XP-002695439; p. 5679-5684.
Garbutt et al., "Properties of Replication-Competent Vesicular Stomatitis Virus Vectors Expressing Glycoproteins of Filoviruses and Arenaviruses," Journal of Virology, vol. 78, No. 10, May 2004, p. 5458-5465, 8 pages.
Johnson et al., "Specific Targeting to CD4 Cells of Recombinant Vesicular Stomatitis Viruses Encoding Human Immunodeficiency Virus Envelope Proteins," Journal of Virology, Jul. 1997, p. 5060-5068, vol. 71, No. 7, 10 pages.
Majid et al., "Evaluating Replication-Defective Vesicular Stomatitis Virus as a Vaccine Vehicle," Journal of Virology, Jul. 2006, p. 6993-7008, vol. 80, No. 14, 17 pages.
Ogino et al., "Use of Vesicular Stomatitis Virus Pseudotypes Bearing Hantaan or Seoul Virus Envelope Proteins in a Rapid and Safe Neutralization Test," Journals.asm.org, Clinical and Diagnostic Laboratory Immunology, Jan. 2003, p. 154-160, vol. 10, No. 1, Received Apr. 5, 2002, 8 pages.
Brown, Kyle S., et al., "Vesicular Stomatitis Virus-Based Vaccine Protects Hamsters Against Lethal Challenge with Andes Virus"; Journal of Virology; vol. 83, No. 23; p. 12781-12791; Dec. 2011.
Fukushi, Shuetsu, et al.; "Vesicular Stomatitis Virus Pseudotyped with Severe Acute Respiratory Syndrome Coronavirus Spike Protein"; Journal of General Virology; vol. 86; p. 2269-2274; 2005.
Hastie, Eric, et al.; "Understanding and Altering Cell Tropism of Vesicular Stomatitis Virus"; Virus Research; vol. 176; p. 16-32; 2013.

(56) References Cited

OTHER PUBLICATIONS

Johnson, J. E., et al.; "A Plasma Membrane Localization Signal in the HIV-1 Envelope Cytoplasmic Domain Prevents Localization at Sites of Vesicular Stomatitis Virus Budding and Incorporation in VSV Virions"; Virology; vol. 251; p. 244-252; 1998.
Saha, Manujendra N., et al.; "Formation of Vesicular Stomatitis Virus Pseudotypes Bearing Surface Proteins of Hepatitis B Virus"; Journal of Virology; vol. 79, No. 19; p. 12566-12574; Oct. 2005.

* cited by examiner

LCMV-GP-VSV-PSEUDOTYPED VECTORS AND TUMOR-INFILTRATING VIRUS-PRODUCING CELLS FOR THE THERAPY OF TUMORS

CROSS REFERENCE TO RELATED APPLICATIONS

The present application is a National Entry of PCT Application No. PCT/EP2009/007230, filed Oct. 8, 2009, which claims priority under the Paris Convention from German Patent Application No. 10 2008 050 860.8, filed Oct. 8, 2008. The entire contents of the aforementioned applications are incorporated herein by reference.

The present invention relates to recombinant viruses derived from the vesicular stomatitis (VSV) and viral vectors which comprise a gene coding for the glycoprotein GP of the lymphocyte choriomeningitis virus (LCMV), packaging cells which produce LCMV-GP-pseudotyped VSV virions, and the use of said virions and packaging cells for the preparation of a pharmaceutical composition for the therapy of solid tumors.

DESCRIPTION OF THE PRIOR ART

Malignant gliomas, the largest group of primary intracranial brain tumors, represent a therapeutic problem which is not solved yet. Although the knowledge of the biology of these tumors has grown due to intense basic research, clinical progress and prognosis are still very poor.

Malignant gliomas are tumors of neuroepithelial origin and are cytologically divided in ependimomas, oligodendro gliomas, oligoastrocytomas, astrocytomas and glioblastomas. With a proportion of more than 60%, diffuse-infiltrating astrocytomas (WHO Grade II-IV) represent the largest group of intracranial tumors. The WHO classification revised in 2001 is largely established as grading scheme for astrocytomas. According to the WHO, brain tumors are allocated by means of histological criteria to 4 malignancy grades (Kleihus and Cavenee, 2000). The prognosis for diffuse-infiltrating astrocytomas is generally poor. The prognosis depends, on the one hand, on the malignancy grade and, on the other, on the localization of the tumor and the therapy procedure. The average survival rate for patients with an astrocytoma WHO grade II is more than 5 years, with an astrocytoma WHO grade III, 2 to 5 years, and with an astrocytoma-glioblastoma of the WHO grade IV (=glioblastoma), less than 1 year.

The molecular pathogenesis of tumors is a complex process and is based on mutations of different genes which are responsible for the control of the cell cycle. Mutations in the tumor suppressor gene p53 are the most frequently found alterations in human tumors and are also responsible for the development of low-grade astrocytomas as well as for the progression to the secondary glioblastoma. However, primary developed glioblastomas very rarely have p53 mutations. A further gene, which indicates a malignant tendency of diffuse astrocytomas, is suspected to be on the long arm of chromosome 19. Further genes which are frequently altered in case of glioblastomas are the oncogenes MDM2 and MDM4 and also the tumor suppressor gene p14ARF, which are involved in the p53-dependent control of the cell cycle (Dai and Holland, 2001). An amplification of the EGF receptor gene is observed in 30-40% of the primary glioblastomas and is therefore the most frequently amplified oncogene in this tumor group (Holland, 2001). The majority of malignant gliomas responds poorly to a chemo- or radiotherapy. It is assumed that the reason for this are mutations of cell-cycle-associated genes which are also involved in the regulation of the apoptosis.

More effective therapy methods for malignant gliomas are urgently needed because from the existing therapy methods such as chemo- or radiotherapy, no significant improvements for the prognosis of the disease are to be expected. In contrast, the gene therapy of the glioblastoma offers promising possibilities which need to be exploited. A plurality of different, very effective genes was developed for this purpose. For most of them, data from experiments on animals are available (Shir and Levitzki, 2001). These therapeutic genes can be allocated to four different active principles:

(i) The gene product of so-called suicide genes converts precursors in cytotoxic molecules. An example is the thymidine kinase (TK) of the herpes simplex virus (HSV) in connection with a dosage of ganciclovir. A particular advantage is that the toxic ganciclovir triphosphate diffuses into adjacent cells, whereby a bystander effect takes place. In the last years, the activity of this enzyme was further increased. HSV TK is currently a very efficient possibility to eliminate tumor cells as well as implanted vector producing cells.

(ii) The expression of immunostimulatory cytokines such as the IL-4 can stimulate the natural defense against tumor cells.

(iii) The secretion of anti-angiogenetic proteins such as the endostatin results in a lack of blood vessels and therefore in a lack of nutrient supply in the metabolically very active tumor tissue. The tumor is virtually "starving".

(iv) Finally, a series of genes was described which engage into the signal transduction or the cell cycle of the tumor cell in order to inhibit the uncontrolled growth of these cells. However, the possibilities of use of these genes in the clinic are limited because these genes act only in the gene-modified cell itself and do not have the bystander effect as the first-mentioned active principles. This means that in order to achieve a therapeutic effect, virtually all malignant cells have to be genetically modified which is hopeless even with ideal vector systems.

The most important prerequisite for a successful gene therapy of the glioblastoma is provided by the multitude of existing, very effective principles of action. However, a problem which is not solved yet is the inefficient gene transfer and a poor expression of the therapeutic gene in the target cells. This is also the reason why, despite the multitude of efficient therapeutic genes, the gene therapy of glioblastoma failed in the clinic.

The advantage of the viral gene transfer over physicochemical transfection methods is the higher gene transfer rate and the long term expression of the genes because the viruses have developed particularly efficient mechanisms to introduce their genome into cells and to express it. In particular replication-competent viruses such as, amongst others, herpes simplex virus (HSV), adenoviruses (Ad), Newcastle Disease Virus (NDV) and the vesicular stomatitis virus (VSV) are currently used as oncolytic viruses (OV). For an optimal virotherapy of glioblastoma, the OV should have the following features:

(i) They should have a tumor-specific tropism, whereby virus replication and cell lysis remains limited to the tumor tissue. This property can be enhanced by modification of the viral envelope or by using tumor-specific promoters. Since the assumption is that only a small portion of the glioma cells divide during the treatment, viruses which infect resting cells as well as proliferating cells are of advantage.

(ii) With respect to safety-relevant aspects, viruses with high genetic stability and a low toxicity outside of the tumor tissue are particularly suitable for clinical use. This allows a high virus titer and a purification of the vectors under GMP conditions. Ideally, the OV should be apathogenic for humans and should have a low infection rate among the population. An already existing immunity would result in a premature neutralization of the virus and thus would not allow an efficient therapy.

Prominent examples for oncolytic viruses in the therapy of glioblastomas are the attenuated HSV variants G207 and 1716 and the adenovirus ONYX-015. A serious objection against the use of oncolytic HSV for the treatment of CNS tumors is its high level replication in normal brain cells which can result in a life threatening encephalitis. Moreover, besides potential persistence, there is the possibility of reactivation of latent HSV. The HSV variant 1716, which was generated by deleting a plurality of genes, selectively replicates in rapidly proliferating cells of the CNS but not in postmitotic neurons. Thereby, the neurotoxicity of HSV was significantly reduced. The treatment of experimental gliomas in the rat and in the mouse with HSV 1716 resulted in selective destruction of tumor cells while surrounding brain tissue remained undamaged. ONYX-015 is a further oncolytic virus which was developed for the glioblastoma therapy. Through a deletion in the E1B gene, this adenovirus is intended to selectively lyse cells with defective p53.

Oncolytic HSV as well as ONYX-015 were already clinically tested for the treatment of gliomas. Both attenuated oncolytic viruses showed a sufficient safety in clinical phase I/II studies. Independently of whether the viruses were injected intratumorally or into the resection cavity, the treatment was well tolerated and no serious side effects were observed. However, the cytolytic effects were only of transient nature, always followed by a recurrence (Cutter et al., 2006). Since normally the proliferation rate of gliomas exceeds the amplification rate and thus the spreading wave of viruses, the destruction of gliomas only by oncolysis is questionable. In fact, for an efficient treatment, the combination of a plurality of active principles is required. By using suicide genes or immunomodulatory genes in OV, a synergistic effect was demonstrated in preclinical studies (Tyminski et al., 2005; Fukuhara et al., 2005).

Besides the aforementioned DNA viruses, oncolytic RNA viruses are also under development. VSV is an enveloped negative-strand virus, the host spectrum of which comprises rodents and livestock. Infections of humans are rare and are mostly asymptomatic. Due to the very low seroprevalence among the population, an impairment of the therapy efficiency by VSV-neutralizing antibodies is not to be expected. The infection and the cytoplasmatic replication of VSV take place independently of the cell cycle so that actively dividing cells and resting cells are equally infected. The efficient and preferential lysis of neoplastic cells by VSV is related to the mostly defective interferon signaling pathway and the accompanying viral replication in these cells (Wollmann et all., 2007). It was also demonstrated that independent of the cellular immune response, tumor cells with defects in the genes Myc, Ras or p53 also support the reproduction of VSV (Barber, 2004). The tumor specificity of VSV was further optimized in the last years by the preparation of recombinant viruses. The main focus here is on variants with mutation in the M protein ($\Delta$M51). This variant is not able to prevent the interferon response in healthy cells, whereby virus replication in such cells is suppressed. In tumor cells with defective IFN response, the virus can replicate and thus be selectively oncolytically active. Even after systemic application, VSV$\Delta$M51 showed a secure and efficient oncolysis of human gliomas in the mouse model (Lun et al., 2006).

The application of viral vectors directly into the brain requires a high selectivity for tumor cells and is only possible in relatively small volumes. Thus, an efficient gene transfer can only be achieved with highly concentrated vector preparations (>108/ml) which have a strongly developed tropism for glioma cells. In case of gamma-retroviral and lentiviral vectors, vector tropism and vector stability can be influenced by integrating a non-retroviral envelope protein. In many cases, the retroviral envelope protein is replaced with the more stable G-protein of VSV. A problem of these so-called pseudotyped vectors is that VSV-G is cell-toxic, namely in the producer cells as well as for the surrounding healthy tissue, which previously stood in the way of a widespread use of such VSV-G pseudotypes in the clinic.

The inventors have previously developed a retroviral vector type which allows for an efficient gene transfer into glial cells of the CNS. In this new vector type, the glycoprotein GP of lymphocyte choriomeningitis virus (LCMV) serves as viral envelope protein (Miletic et al., 1999; Beyer et al., 2002; EP 1 006 196). In comparative in vitro and in vivo tropism studies it was demonstrated that LCMV-GP pseudotypes transduce preferentially glioma cells (Miletic et al., 2004; Miletic et al., 2007). In contrast to that, VSV-G pseudotypes preferentially transduced neurons; whereas gene transfer in glioma cells was less efficient than with LCMV-GP pseudotypes. Also individual infiltrating tumor cells were efficiently transduced by LCMV-GP pseudotypes. In the rat glioma model, 90% of the rats were healed by intratumoral injection of LCMV-GP-pseudotyped lentiviral vectors (Miletic et al.; 2007b). The used vectors coded for the thymidine kinase (TK) of the herpes simplex virus, with the effect that in the transduced cells as well as in the surrounding cells, ganciclovir was converted into a cell-toxic triphosphate compound.

The selective gene transfer into gliomas, but also an efficient vector distribution within the entire tumor are decisive for the success of the therapy. Therefore, the inventors have developed tumor-infiltrating packaging cells which are supposed to release pseudotyped vectors within the entire tumor (WO 2006/008074). A promising cell type with migratory capabilities is the multipotent, adult progenitor cell which can be isolated from the bone marrow (Jiang et al., 2002). In transplantation experiments, the migration behavior of these cells was examined using the rat glioma model. It was demonstrated that the progenitor cells efficiently penetrated the tumor mass, but did not infiltrate the surrounding healthy brain tissue (Fischer et al., 2007). Conventional cell lines such as 3T3 mouse fibroblasts, Rat-1 rat fibroblasts or human 293T did not show any tumor infiltration. Rather, these cells were locally limited to the injection site or the vicinity and did not show glioma-specific migration.

In a further study, the inventors examined the therapeutic efficacy of TK-expressing progenitor cells in the rat glioma model. The result of this study was that in 70% of the rats the destruction of the tumor was solely due to the bystander effect between progenitor cell and tumor cell (Miletic et al., 2007). Moreover, the intratumoral localization of the progenitor cells by means of imaging methods was confirmed. Histological slices of the brain of treated, symptom-free rats had a cavity with a pronounced scar tissue at the location of the tumor; this indicates that the tumor in the animals was successfully eradicated by the gene therapy. Thanks to the strong expansion potential of these progenitor cells, a genetic modification with subsequent selection of individual packaging cell clones is possible. A progenitor-based packaging cell for gamma-retroviral LCMV-GP pseudotypes was developed. These packaging cells continuously produced retroviral vectors with a titer of 1-7x10E3 TU/ml. The titers remained stable over several weeks and after repeated freezing and thawing the cells (Fischer et al., 2007).

The inefficient gene transfer in vivo and not the lack of therapeutically effective genes currently hinders successful gene therapy of the glioblastoma. The previously known vectors for gene therapy and oncolytic virotherapy of gliomas are not optimal for various reasons. The efficiency, specificity and safety of previous gene transfer methods are to be increased to such an extent that a therapeutically effective gene transfer in patients is possible.

It is therefore the object of the present invention to develop a highly potent oncolytic viral gene transfer system for therapeutic genes for the therapy of highly malignant brain tumors such as gliomas and other solid tumors.

SUMMARY OF THE INVENTION

The subject matter of the invention is therefore a vesicular stomatitis virus (VSV) pseudotype vector which comprises a gene coding for glycoprotein GP of lymphocyte choriomeningitis virus (LCMV) and no functional gene coding for envelope protein G VSV. In the following, the vector of the invention will be referred to as VSV-LCMV-GP pseudotype vector. GP of LCMV (LCMV-GP) can be glycoprotein GP-1 or GP-2 of LMCV.

According to a further embodiment, in the VSV-LCMV-GP pseudotype vector, the envelope protein G of VSV is replaced by GP of LCMV (LCMV-GP).

According to a further embodiment, the vector lacks at least one gene selected from the group of n, l, p and m genes coding for proteins N, L, P and M of VSV.

According to a further embodiment, the M protein of VSV comprises mutations which reduce the cytopathogenicity of VSV. Examples of mutations resulting in reduced cytopathogenicity of VSV are amino acid exchanges in the 37PSAP40 region of the M protein as well as mutations M33A, M51A, V221F, S226R or their combination.

According to a further embodiment, the VSV-LCMV-GP pseudotype vector comprises at least one therapeutically applicable transgene. The transgene can be a suicide gene or an immunostimulatory gene. Examples of suicide genes are genes which code for thymidine kinase of the herpes simplex virus (HSV-TK), cytosine deaminase, FKBP-FAS or FKBP-caspase 9. Examples of immunostimulatory genes are genes which code for cytokines IL-2, IL-4, IL-12, neutralizing anti-TGFbeta, or Flt3L.

According to a further embodiment, the VSV-LCMV-GP pseudotype vector comprises a marker gene. The marker gene can be LacZ, an antibiotic resistance gene or a gene coding for fluorescence protein (GFP, RFP, GGP etc.).

The subject matter of the invention is further a VSV-LCMV-GP pseudotype vector system which comprises at least two complementary replicating (cr) VSV vectors, wherein one vector of the vector system comprises a gene gp coding for LCMV-GP, wherein the vector system further comprises genes n, l, p and m coding for proteins N, L, P and M of VSV and no functional gene coding for envelope protein G of VSV, wherein each vector of the vector system lacks one of the genes ("complementary gene") gp, n, l, p and m, and wherein the lacking gene is present on any other vector of the vector system. The genes m and gp are preferred complementary genes.

According to a further embodiment, the M protein of the VSV-LCMV-GP pseudotype vector system comprises mutations which reduce the cytopathogenicity of VSV, as indicated above.

According to a further embodiment, the VSV-LCMV-GP pseudotype vector system comprises at least one therapeutically applicable transgene and/or a marker gene, as indicated above. The transgene/marker gene can be located on any vector of the vector system.

The subject matter of the invention is further a VSV virion pseudotyped with LCMV-GP which comprises a glycoprotein GP of LCMV as envelope protein.

The subject matter of the invention is further a virus producing cell which produces a VSV virion pseudotyped with LCMV-GP.

According to a further embodiment, the virus producing cell is an adult stem cell. The adult stem cell can be a multipotent adult progenitor cell (MAPC), a neuronal stem cell (NSC), a mesenchymal stem cell (MSC) or a BM-TIC cell (bone marrow derived tumor infiltrating cell) derived from MSC.

According to a further embodiment, the virus producing cell comprises one or more expression cassettes for the expression of genes selected from the group consisting of the genes n, l, p and m coding for proteins N, L, P and M of VSV, respectively, and a gene gp coding for LCMV-GP glycoprotein.

According to a further embodiment, the virus producing cell further comprises a gene transfer vector for packaging into a VSV virion pseudotyped with LCMV-GP.

According to a further embodiment, the gene transfer vector comprises a therapeutically applicable transgene and/or a marker gene, as indicated above.

The subject matter of the invention is further an in vitro method for transferring a transgene into cell, in which method the cell is transduced with a VSV virion pseudotyped with LCMV-GP, wherein the virion comprises a transgene.

The subject matter of the invention is further an in vitro method for transferring a transgene into a cell, in which method the cell is contacted with a virus producing cell which produces a VSV virion pseudotyped with LCMV-GP, wherein the virion comprises a transgene.

It is preferred that the cell is a tumor cell, for example, a glioma cell.

The subject matter of the invention is further the use of a VSV-LCMV-GP pseudotype vector or a VSV-LCMV-GP pseudotype vector system of the invention for the preparation of a pharmaceutical composition for the therapy of a solid tumor.

The subject matter of the invention is the use of a VSV virion pseudotyped with LCMV-GP for the preparation of a pharmaceutical composition for the therapy of a solid tumor.

The subject matter of the invention is further the use of a virus producing cell of the invention for the preparation of a pharmaceutical composition for the therapy of a solid tumor. It is preferred that the tumor is a brain tumor, in particular a glioma.

According to a further embodiment, at least two virus producing cells are used for the preparation of a pharmaceutical composition for the therapy of a solid tumor, wherein a first virus producing cell comprises a first vector of the VSV-LCMV-GP pseudotype vector system and a second virus producing cell comprises a second vector of the VSV-LCMV-GP pseudotype vector system.

Furthermore, subject matter of the invention is a pharmaceutical composition which comprises a VSV-LMCV-GP pseudotype vector, a VSV-LCMV-GP pseudotype vector system, a VSV virion pseudotyped with LCMV-GP, or a virus producing cell which produces a VSV virion pseudotyped with LCMV-GP. The composition can also comprise suitable auxiliary substances and/or carriers.

Figure 5:
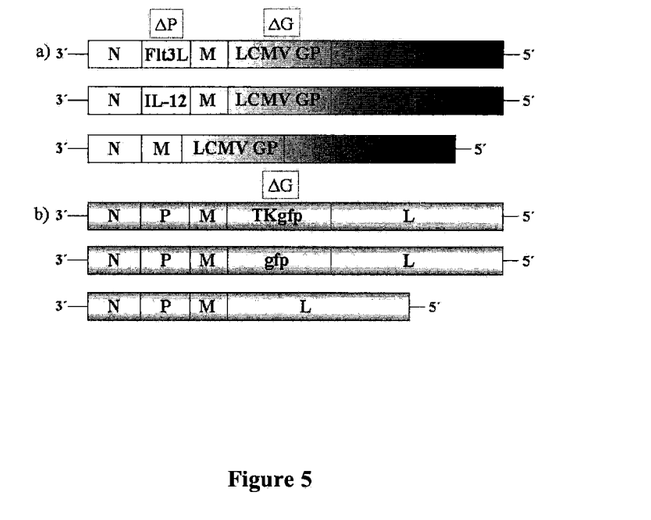

Different variants of the vector system according to the invention are possible. For example, the vector system can consist of two vectors as illustrated in FIG. 5. A first vector comprises GP of LCMV instead of G of VSV and a deletion of the gene p coding for the P protein. Also a second vector comprises no VSV-G but expresses the P protein of VSV. Each vector expresses nucleoprotein (N) and polymerase (L) of VSV as well as a less cytopathogenic variant of the M protein (Mncp). The first vector carries in addition the marker gene rfp, whereas the second vector carries the suicide gene HSV-TK and the marker gene gfp. In the variants illustrated in FIG. 6, both vectors can comprise a therapeutic gene, wherein the first vector comprises, e.g., Flt3L or IL-12 and the second vector comprises, e.g. HSV-TK.

Up to now, different concepts for the therapy of the glioblastoma have been pursued: (i) the transfer of suicide genes, (ii) the elimination of the glioblastoma-related immunosuppression using immunostimulatory genes and by means of cytokine-based immunotherapy, (iii) the transfer of factors which counteract the tumor-induced angiogenesis, (iv) the use of cell cycle modulators and (v) the induction of apoptosis. For the purposes of the invention, the first three approaches (i-iii) are to be primarily considered.

In addition to their inherent oncolytic properties, the VSV-LCMV-GP pseudotype vectors and vector systems based thereon can further be improved by introducing suicide genes or/and immunostimulatory genes. Examples of suicide proteins are thymidine kinase of the herpes simplex virus (HSV-TK), cytosine deaminase, FKBP-FAS, FKBP-caspase9. Examples of immunostimulatory proteins are cytokines such as IL-2, IL-4, IL-12 and Flt3L, neutralizing anti-TGFbeta. Insertions of genes with a size of up to 4.5 kb are tolerated by the VSV genome so that it would even be possible to combine two or more therapeutic genes (e.g. HSV-TK+cytokine) in one VSV genome. In addition, the gene products exert their action also on non-infected tumor cells by means of a so-called bystander effect.

Injected viral vectors penetrate from the injection site only a few millimeters into the tumor tissue. For optimizing the vector distribution and for the targeted destruction of the tumor, tumor-infiltrating virus producing cells are used which specifically migrate in the tumor thereby releasing the viruses at the site remote from the injection site.

Virus producing cells in the meaning of the invention include classical packaging cells for the production of virions from non-replicable vectors as well as producer cells for the production of virions from vectors capable of reproduction. Packaging cells usually comprise one or more plasmids for the expression of essential genes which lack in the respective vector to be packaged and/or are necessary for the production of virions.

In previous studies, packaging cells were used for transferring viral vectors; however, this involved mainly fibroblasts which do not migrate within the tumor (Short et al., 1990, Culver et al., 1992). In contrast, adult stem cells, in particular neuronal (NSC) and mesenchymal stem cells (MSC) have a high migratory potential. They remain confined to the tumor tissue, whereby a very efficient but also specific gene transfer into the tumor tissue is achieved. However, these stem cells have limited passage capacity in vitro.

A subpopulation of adult mesenchymal stem cells, so-called BM-TIC (bone marrow derived tumor infiltrating cells) infiltrate, after injection into experimentally induced gliomas, the entire tumor and, in addition, track individual tumor cells remote from the tumor mass (Miletic et al., 2007). BM-TIC are isolated from adult bone marrow, have a high expansion potential and can be used as migrating producer cells for MLV (Fischer et al., 2007) and VSV vectors.

The subject matter of the invention is thus virus producing cells which produce oncolytic VSV-LCMV-GP pseudotype vectors. In particular, these are tumor-infiltrating producer cells which release the said vectors during their migration within the tumor. Preferred cells are adult stem cells, in particular neuronal (NSC) and mesenchymal stem cells (MSC). Particularly preferred cells are BM-TIC cells derived from MSC.

An obstacle for the preparation of a rhabdoviral virus producing cell is the cytopathogenicity of the proteins M and G. Since the G protein of VSV is replaced by the glioma-specific and non-cytotoxic glycoprotein of LCMV in the VSV-LCMV-GP pseudotype vectors of the invention, only the M protein remains a problem. For reducing the toxicity of the M protein in the VSV producing cell line, a non-cytopathogenic variant of the M protein can be used.

Therefore, the virus producing cells of the invention and hence also the VSV-LCMV-GP pseudotype vectors produced by said cells may comprise a gene coding for a mutated M protein. This vector variant is selectively oncolytic for tumor cells, whereas it is not toxic for healthy cells. M variants with amino acid exchange in the 37PSAP40 region of the M protein or with single (M51R) or multiple (V221F and 5226R; M33A and M51A) mutations outside of the PSAP region of the M protein are preferred. An M protein with mutations M33A, M51R, V22F and S226R is particularly preferred. In order to ensure an efficient virus production in packaging cells, the M variant can be stably transfected with a viral interferon antagonist.

In addition, subject matter of the invention is an in vitro method for gene transfer, wherein a VSV-LCMV-GP pseudotype vector or VSV-LCMV-GP pseudotype vector system comprising a transgene is introduced into a cell either directly or by means of virus producing cells (packaging cells) according to the invention. If a complementary replicating (cr) vector system with at least two vectors is used, at least two packaging cells are used, wherein each of the cells produces one of the (replication-incompetent) cr vectors. The production of VSV viruses takes place only in cells which are infected with all vectors of the cr vector system and hence comprise all essential viral genes.

In addition, the invention relates to the use of vectors and virus producing cells according to the invention as drugs in therapeutic methods. In particular, the vectors and virus producing cells according to the invention are used for the therapy of solid tumors. The therapeutic effect is caused by the oncolytic properties of the recombinant vectors and viruses as well as by the use of therapeutic genes.

Solid tumors can be brain tumor, liver tumor, in particular hepatocellular carcinoma, lung tumor, in particular bronchial carcinoma, and intestinal tumor, in particular colon carcinoma. Preferred tumors are brain tumors, for example a glioma, in particular ependymoma, oligodendroglioma, oligoastrocytoma, astrocytoma, glioblastoma, or a medulloblastoma.

The subject matter of the invention is further a pharmaceutical composition which comprises the vector, the virion, the virus producing cell of the invention and optionally additives such as carrier and auxiliary substances.

In order to increase the viral oncolysis and the transfer efficiency of the therapeutic genes, tumor-infiltrating virus producing cells which continuously release vectors are formulated for direct implantation into the tumors.

The invention is illustrated by means of the following examples.

EXAMPLES

Example 1

Transduction of Glioma Cells by VSV-LCMV-Pseudotype Vectors

Figure 1:
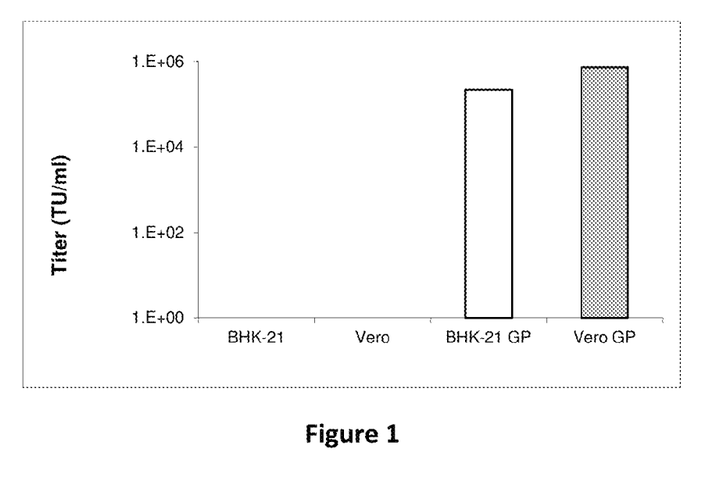
FIG. 1: Pseudotyping of VSVgfp ncp-ΔG vectors with LCMV GP

Defective VSV vectors which encode GFP but no viral envelope protein (VSVgfp-ncp-ΔG) were transduced into BHK-21 and vero cells which in turn stably express GP of LCMV. 1x10E5 cells (BHK-21, -GP, vero, -GP) were sown per 24-well plate cavity and four hours later transduced at MOI=5 with VSVgfp-ncp-ΔG vectors. 24 hours later, the culture supernatant was collected and the titer in BHK-21 was determined by means of FACS analysis of the GFP expression. FIG. 1 shows that the transduced cells produced LCMV-GP-pseudotyped VSV vectors, wherein depending on the used cell type, the pseudotype titers varied between 2-7x10E5 TU/ml.

Figure 2:
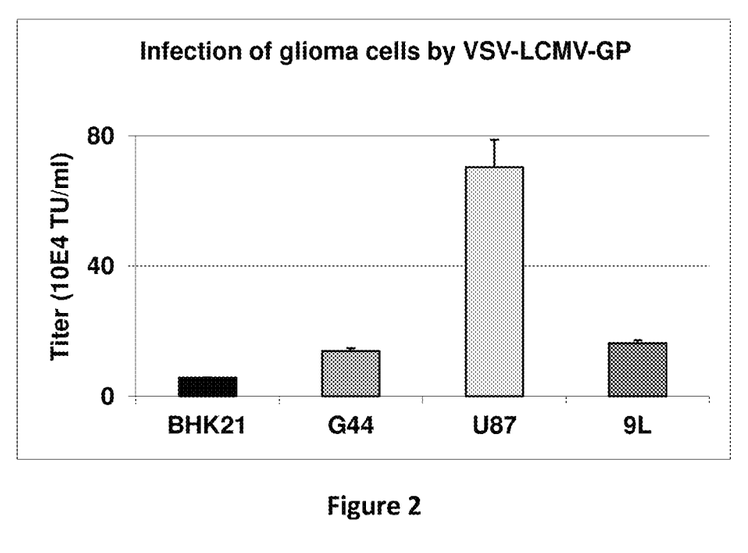
FIG. 2: Transduction of glioma cell lines with VSV-LCMV-GP vectors

Since the pseudotypes were intended for the gene transfer in gliomas, the transduction efficiency of the vectors was checked for different glioma cell lines. Two human glioma cell lines (U87, G44) and a rat glioma cell line (9 L) were tested. BHK-21 were used again as a control. 1x10E5 cells per 24-well plate cavity were seeded and four hours later transduced at MOI=0.3 (titration on BHK-21) with VSV-LCMV-GP pseudotype vectors. 24 hours later, the percentage of GFP-expressed cells was determined by FACS and the titer was calculated therefrom. FIG. 2 shows that the glioma cell lines were efficiently transduced by LCMV-GP-pseudotyped VSV vectors.

Example 2

Packaging of VSV-LCMV-GP Pseudotype Vectors in Multipotent Progenitor Cells

Figure 3:
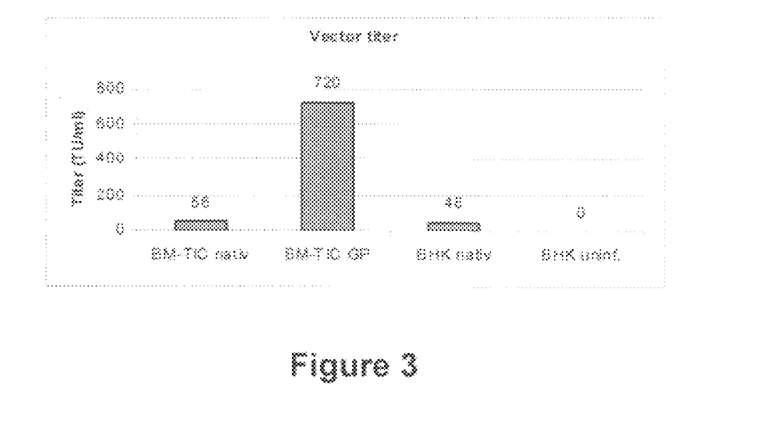
FIG. 3: Pseudotyping of VSVgfp ncp-ΔG vectors with LCMV-GP in BM-TI however, is present on any other vector of the system. The gene gp coding for LCMV-GP as well as possible additional genes such as therapeutic genes and/or marker genes can be present on any vector of the system.

The inventors have already demonstrated that stem cells which were isolated according to the protocol of C. Verfaillie (Jiang et al., 2002), have tumor-infiltrating properties. Because only their migration potential but not their differentiation potential was examined, these cells were called BM-TIC (bone marrow derived tumor infiltrating cells). For testing the packaging capability of BM-TIC for VSV vectors, LCMV-GP-expressing BM-TIC were transduced with the defective VSV-GFP vector. 1x10E5 cells (BM-TIC, -GP, BHK-21) were seeded per 24-well plate cavity and four hours later transduced at MOI=5 with VSVgfp-ncp-ΔG vectors. 24 hours later, the culture supernatant was collected and titrated on BHK-21 cells. FIG. 3 shows that VSV-LCMV-GP pseudotypes can also be prepared in BM-TIC. However, the titers are lower as for example with BHK-21 cells (see FIG. 1).

Example 3

Development of Complementary Replicating (Cr) VSV-LCMV-GP Pseudotype Vectors

A high transduction rate can be achieved with viruses capable of reproduction. In order to increase the gene transfer rate in gliomas and at the same time to ensure a high degree of safety, a VSV pseudotype vector was established which is replication-competent to a limited extent. Systems with complementary defective viruses have been described for retroviruses (Trajecevski et al., 2005) and different flaviviruses (Riepl & Mandl, 2007). The principle of such systems is to distribute the viral genome between two incomplete replicons. Infectious viruses are only produced if one and the same cell is infected with both vectors and only through this co-infection comprises all the necessary components for packaging the virus genome.

Figure 4:
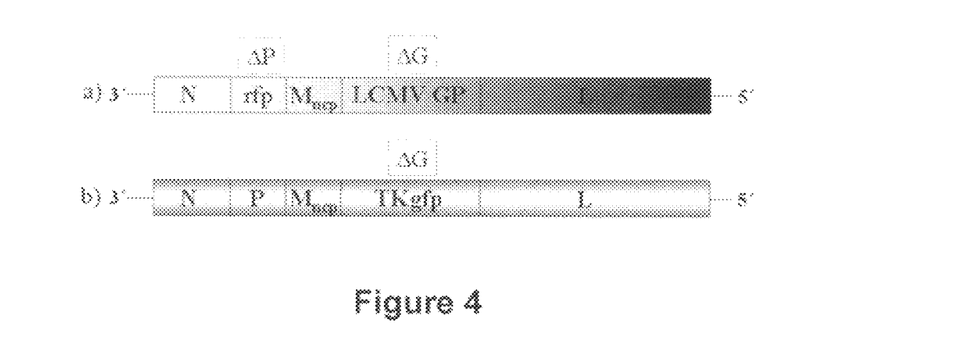

FIG. 4 shows an example of complementary vectors of the vector system according to the invention. For an efficient replication and packaging, the first vector lacks the phosphoprotein P. In order to be able to determine the viral titer of these vectors in a simpler manner, the vector encodes the red fluorescent protein (rfp) instead of P. The lacking P function is complemented during the co-infection of the cell by the second vector. However, the latter alone is not capable of reproduction because it lacks the essential envelope protein VSV-G. By means of this vector, therapeutic genes are applied.

While only the genomic RNA of positive-strand RNA viruses is infectious, negative-strand RNA viruses such as the VSV need in addition to the viral RNA genome at least viral nucleoprotein (N) and viral polymerase (L) in order to generate an infectious virion from cloned viral cDNAs. The system for preparing recombinant VSV is based on the cytoplasmatic expression of viral (+)RNA and the viral proteins N, P and L using the T7-RNA polymerase which is constitutively expressed in BSR T7/5 cells. In order to prepare the desired vectors, genomic constructs together with the expression plasmids for N, P and L and additionally the expression plasmid for VSV-G in the case of Vector b) (FIG. 4) are co-transfected into the BSR T7/5. The titers can be considerably increased by passaging the viruses obtained in this manner on cells which express the lacking component in trans. For the LCMV-GP-deficient vector, a BHK-21 cell line which stably expresses GP was established. For the P-deficient vector, a BHK-21 cell line which expresses the P protein was established.

Preparation and Characterization of Cr VSV-LCMV-GP Pseudotype Vectors

After characterization of the individual vectors with respect to their titer and their transduction efficiency, the spread of the vectors in vitro is examined. For this, BHK-21 cells are co-infected with both vectors and the replication and thus the generation of new vectors by serial passage of the culture supernatant on native BHK-21 is examined. These experiments are repeated with different glioblastoma cell lines (G44, G62, U87) which are cultivated as monolayer as well as spheroids.

Tumor spheroids are three-dimensional, organoid cell groups which reflect the nature and heterogeneity of tumors better than monolayer cultures. The actively dividing tumor cells are located in a loose formation at the edge of the cell aggregate, whereas cells located deeper inside no longer divide and a formation of necrotic areas takes place here (Carlsson et al., 1984). Experiments with spheroids provide information about intratumoral transduction efficiency, the spreading kinetics and the oncolytic effect of the cr VSV-LCMV-GP pseudotype vector system. These spheroids thus allow an initial optimization of the system without the need of conducting experiments in animals. A possible toxicity of the cr LCMV-GP-pseudotyped VSV vectors, the therapeutic effectiveness of the oncolysis and the presence of the remaining viruses after tumor elimination are examined in the animal model (see Example 6).

The viral RNA polymerase has no recombinase activity and there are also no cellular recombinases in the cytoplasm so that the recombination between two negative-stranded RNA viruses can only take place by a template switching of the RNA polymerase. However, this is an extremely rare event (Finke & Conzelmann, 2005; Spann et al., 2003). The generation of a recombinant, replicable VSV represents a safety risk and is examined. For this, viral RNA is isolated at different times from the culture supernatant of co-infected cells and examined with a transgene-specific (e.g. gfp) probe in Northern blots. If RNA species with "excess length" are detectable, the viruses from the supernatant are plaque-purified and examined by means of standard methods with respect to their infectivity and are subsequently characterized by means of molecular biology.

Example 4

Establishment of a Migrating Producer Cell for the Preparation of Therapeutically Effective VSV-LCMV-GP Pseudotype Vectors Migrating VSV-LCMV-GP producer cells are established for cr VSV vectors and for replication-competent VSV-LCMV-GP vectors.

Preparation and Characterization of Different M Variants

The VSV M protein has two essential tasks within the VSV cycle. On the one hand, it is essential as structural component of the virion for the assembly and the sprouting of the viruses. On the other hand, it contributes significantly to the viral pathogenesis through its "host shut-off" activity directed to the host protein synthesis and through induction of the apoptosis. In this connection, an important function of M is the inhibition of the nucleo-cytoplasmatic transport of IFN mRNA. Thereby, the first defense mechanism of the cell against viral infection is suppressed.

Due to this strong cytotoxic effect, it is not possible to express the M protein in cell lines on a long-term basis. However, a plurality of mutations in the M protein is known which result in the attenuation of the virus. Irie and coworkers demonstrated that by amino acid exchanges in the so-called 37PSAP40 region of the M protein, a VSV mutant with greatly reduced cytopathogenicity was created (Irie et al., 2007). Furthermore, as shown in mouse experiments, M variants with single (M51R) or multiple (V221F and S226R; M33A and M51A) mutations outside of the PSAP region are also greatly attenuated (Desforges et al., 2001; Jayakar and Whitt, 2002). These viruses are not able to suppress the release of IFN-α/β and accordingly induce an antiviral status which protects the animals against an infection. However, in tumors which often have defects in the IFN system, these viruses can reproduce and lyse the tumor. For safety reasons, such attenuated variants are of particular importance for the gene therapy because they replicate preferentially in tumor cells.

Also, the inventors have cloned a non-cytopathogenic variant of the M protein (Mncp) which comprises the mentioned mutations M33A, M51R, V221F and S226R and is no longer able to suppress the synthesis of IFN-β. This variant replicates in a similar efficient manner as the parent virus on IFN-incompetent cells, but is attenuated on IFN-competent cells. To ensure efficient virus production in BM-TIC, the cells are stably transfected with a viral interferon antagonist (Haller et al., 2006).

Preparation and characterizing of a BM-TIC-derived producer cell for VSV-LCMV-GP pseudotype vectors Tumor cells are primarily transduced due to the glioma-specific tropism of the VSV-LCMV-GP pseudotypes. Therefore, it is possible to also work with M variants which still show certain cytopathogenicity. In order to keep the toxic effects in BM-TIC low, the antiviral MxA protein should be expressed in the cells via a Tet-inducible promoter. Retroviral vectors with Tet-inducible promoter are known (Loew et al., 2006). The Tet-responsive element (tTA) is also introduced into BM-TIC via a retroviral vector. MxA is an interferon-induced GTPase with antiviral activity towards RNA viruses (Pavlovic et al., 1992; Stäheli and Pavlovic, 1991). In the cytoplasm it is present in the form of large oligomers, is not toxic and inhibits the replication of VSV by a hitherto unknown mechanism. LCMV-GP expressing BM-TIC are transduced with the Tet-regulated MxA and the tTA vector and subsequently infected with the VSV vectors. As long as the antibiotic is present in the medium, the cells are resistant against a productive infection with VSV (LCMV-GP) due to the presence of MxA. Only during the in vivo application, the antibiotic is removed and a viral replication and production of VSV (LCMV-GP) gradually begins. Since MxA with a half-life of two days is very stable, the mutant MxA(L612K) can alternatively be used. MxA(L612K) inhibits the infection of VSV with the same effectiveness as the wild-type protein, but is not able to form oligomers. Hereby it is destabilized and has a short half-life of only two hours (Janzen et al., 2000).

Both producer cells, BM-TIC which produce vectors with non-cytopathogenic M as well as BM-TIC which are protected against VSV-related lysis through MxA expression, are characterized as follows:

(i) The vector titers and the duration of the vector production are determined.
(ii) The influence of freezing and thawing of the cells on the vector titer is analyzed.
(iii) Whether the cells still have tumor-infiltrating properties and which transduction efficiencies are achieved in the tumor tissue is analyzed first in the spheroid model and subsequently in the animal model.
(iv) The produced vector supernatant is checked for the presence of replicable VSV.

Example 5

Cloning and Packaging of Therapeutic Genes

A suicide gene can be used as therapeutic gene according to the invention. An example of such a gene is the thymidine kinase of the herpes simplex virus (HSV-TK) with the most experience in the clinic. Through the constitutive expression of the HSV-TK, packaging cells and transduced cells can be reliably eliminated at the end of the therapy so that no danger can arise from mitotically active packaging cells.

For the immunotherapy of malignant gliomas, i.e., for strengthening the poorly developed local immune response in the brain, immunomodulatory genes can be used. Examples of such genes are cytokines, in particular IL-12 and Flt3L. After antigen stimulation, IL-12 is naturally secreted by antigen-presenting cells such as dendritic cells, macrophages and B cells and mediates a strong Th1-based anti-tumor immune response. It enhances the growth and the differentiation of naive T cells into Th1 cells and thus counteracts a glioma-induced suppression of the T cell proliferation and IFN-gamma production. IL-12 enhances the cytotoxic activity of natural killer and CD8+ cells and has in addition an anti-angiogenic activity (Majewski et al., 1996). In a plurality of animal models, the effectiveness of an IL-12-mediated immune response against gliomas has already been demonstrated in an impressive manner (Toda et al., 1998; Kikuchi et al., 1999). The cytokine Flt3L is essential for the proliferation and differentiation of antigen-presented dendritic cells and thus seems to be particularly well suited for the purposes of a gene therapy. Sumia and colleagues observed in the rat/mouse a strong local influx of dendritic cells after i.c. transduction of gliomas with the Flt3L gene. 70% of the treated rats showed tumor regression and survived.

The combination of a cytokine with a suicide gene (TK) does not only offer maximum safety, but also allows a successful therapy with low transduction efficiency due to the bystander effect. This approach combines three active principles, namely viral oncolysis, suicide gene-induced apoptosis and local immunostimulation in order to increase the efficiency of the gene therapy of the glioblastoma.

First, 11-12 and Flt3L are cloned into the VSV vectors. IL-12 is species-specifically active so that the murine IL-12 has to be used for testing in the rat glioma model. In contrast, more than 70% of human and murine Flt3L are homologous and are cross-reactive in both species. The immunostimulatory genes are cloned into the position of the p gene, whereas TKgfp or gfp on the second vector replaces the VSV-G gene. The following gene combinations are cloned into the two vectors of the cr VSV-LCMV-GP pseudotype vector system (FIG. 5):
 1) vector a=IL12 or Flt3L+vector b=TKgfp (or TK)
 2) vector a=IL12 or Flt3L+vector b=gfp
 3) vector a=IL12 or Flt3L+vector b=empty
 4) vector a=empty+vector b=TKgfp (or TK)
 5) vector a=empty+vector b=gfp
 6) vector a=empty+vector b=empty After cloning, glioma cell lines and BM-TIC are transduced and the concentration of the cytokine contained in the supernatant is verified by ELISA. For the production of physiologically relevant amounts the vectors are concentrated via ultracentrifugation. The vectors are first used for the transduction of spheroids and their competence to bystander killing is examined in this system. Afterwards, the vector supernatants together with the prepared packaging cells are sent to Bergen to our cooperation partner. There, the in vivo testing in the syngeneic rat glioma model takes place. The survival rate of the treated rats after ganciclovir application is evaluated. At the same time, the therapeutic effectiveness of the immunotherapy in the absence of TK is examined. The vector combination 6) provides information about the effectiveness of the oncolysis. Tumor size and thus the therapy success are monitored via MRI and PET (Miletic et al., 2007). The effect of the immunomodulatory genes is evaluated by means of immunohistochemical methods for detection of infiltrate cells. As described in the following paragraph, the therapeutic approach is also examined in the human glioma model.

Example 6

Testing of the Therapeutic Active Principle in Two Glioma Models

The recombinant VSV vectors are first characterized in vitro and are subsequently investigated in the animal model for their effectiveness. For this purpose, two particularly meaningful rat models are used.

A syngeneic 9 L rat glioma model is used for the examination of immunological aspects and the carrying out of immunotherapeutic methods. For this purpose, glioma cell lines are implanted into the brains of Fisher rats which subsequently develop tumors within a few days. 9 L gliosarcoma cells which were isolated from Fisher rats served as tumor cell lines. Various vectors or cell lines are then stereotactically injected into the induced tumors. This rat model has the following characteristics:
 (i) It represents a well reproducible system with a low inter-individual variance.
 (ii) The tumors have characteristics similar to human gliomas such as, e.g., the invasive and aggressive growth behavior as well as the production of TGFβ2 as immunosuppressive factor.
 (iii) In contrast to the SCID/nude mouse model or the rat xenograft model, the system allows the examination of immunological aspects or the testing of immunotherapeutic methods.

A human glioma model in nude rats is used for testing the oncolytic activity of the vectors and cells according to the invention towards human glioma cells. The rat xenograft model simulates various growth characteristics of human gliomas. Not a defined glioblastoma cell line but primary tumor material from patients is used here for establishing the tumor, which allows to simulate the heterogeneity within human gliomas (Sakariassen et al., 2006). By the serial passage of human gliomas in nude rats, different phases of the malignant tumor development can be mapped and the therapy success can be examined. The human glioma model is particularly well suited for the examination of therapeutic approaches because it has the following characteristics:
 (i) The tumors have similar characteristics to human gliomas such as, e.g., the invasive and aggressive growth behavior. Not a glioma cell lines but primary patient material is used for establishing the tumors.
 (ii) Through the serial passage of tumors, different phases of the development of a malignant tumor can be mapped and the success of therapy can be verified. Tumors of the first generation grow slowly, are highly invasive and have a low neurovascularization. A greatly vascularized phenotype with strong proliferation and reduced invasion develops through passaging.
 (iii) The cellular phenotype of highly invasive, non-angiogenetic gliomas is similar to the one of tumor stem cells. Thus, this animal model allows the testing of the therapeutic effectiveness of our concept on the stem cell component of the human GBM.

Two categories of tumors can be distinguished:
 (i) Early tumors with a slow, highly invasive growth behavior. These tumors have only a low vascularization.
 (ii) Late tumors which are well supplied with blood and grow fast. This phenotype is poorly invasive.

The human glioma model is very well suited for examining suicide gene therapy as well as the viral oncolysis. However, up to now there are no animal models for the human glioblastoma which can be used for the analysis of the immunotherapeutic effectiveness of gene therapeutic methods.

The success of therapy is analyzed and evaluated by means of imaging methods and finally with histological techniques. First, the mode of action of the complementary replicating VSV(LCMV-GP) pseudotypes is examined by intratumoral injection of concentrated vector supernatants in the rat glioma model. The transduction efficiency and the distribution of the gfp-coding vectors within the tumors are examined after a few days by means of a fluorescence microscopic analysis of frozen sections. Furthermore, oncolysis and the invasion of immune cells are immunohistochemically evaluated. As a supplement, the effectiveness is also examined in the animal model for the human glioblastoma.

In the same model, the migration capability of the BM-TIC producer cells and the infectivity of the produced VSV vectors are examined. For this purpose, the cells are stained with a green dye whereas the released vectors code for rfp. This approach allows a simple fluorescence-based differentiation between BM-TIC and transduced tumor cells.

Finally, the therapeutic efficiency of the individual transgene-coding pseudotypes is compared. For this purpose, the packaging cells and also the concentrated vector supernatants are injected into established 9 L tumors. The vectors comprise an immunostimulatory gene in combination with TK. Ganciclovir administration begins a few days after the stereotactical application of the vectors or the packaging cells. The therapeutic efficiency of the immunomodulatory component of the vector is evaluated in animals that receive vectors containing only TK. Upon completion of the treatment, the effectiveness of the individual therapy concepts is evaluated based on the tumor size with imaging methods (MRI; PET). A portion of the brains of rats treated with immunotherapy is used for characterizing the immune status. The expression of MHC molecules and the distribution of T cells, granulocytes, macrophages and microglial cells are examined on the frozen sections by immunohistochemical methods. In addition, the quantity and phenotypical composition of the i.c. infiltrate cells are analyzed by flow cytometry. The formulation with the best therapeutic effect is adapted for the treatment of human gliomas. Such a prototype could be transferred directly into preclinical safety studies and, after establishing the respective methods for GMP production, into clinical studies.

LITERATURE

1. Barber G N. Vesicular stomatitis virus as an oncolytic vector. Viral Immunol. 2004; 17(4):516-27
2. Beyer W R, Westphal M, Ostertag W, von Laer D. Oncoretrovirus and lentivirus vectors pseudotyped with lymphocytic choriomeningitis virus glycoprotein: generation, concentration, and broad host range (2002). J Virol. 76:1488-95
3. Carlsson J, Yuhas J M. Liquid-overlay culture of cellular spheroids. Recent Results Cancer Res. 1984; 95:1-23
4. Culver K W, Ram Z, Wallbridge S, Ishii H, Oldfield E H, Blaese R M. In vivo gene transfer with retroviral vector-producer cells for treatment of experimental brain tumors. Science. 1992 Jun. 12; 256(5063):1550-2
5. Cutter J L, Kurozumi K, Chiocca E A, Kaur B. Gene therapeutics: the future of brain tumor therapy? Expert Review of Anticancer Therapy; 2006, 6(7): 1053-1064
6. Dai C, Holland E C. Glioma models. Biochim Biophys Acta. 2001 Aug. 31; 1551(1): M19-27
7. Desforges M, Charron J, Berard S, Beausoleil S, Stojdl D F, Despars G, Laverdiere B, Bell J C, Talbot P J, Stanners C P, Poliquin L. Different host-cell shutoff strategies related to the matrix protein lead to persistence of vesicular stomatitis virus mutants on fibroblast cells. Virus Res. 2001 July; 76(1):87-102
8. Finke S, Conzelmann K K. Recombinant rhabdoviruses: vectors for vaccine development and gene therapy. Curr Top Microbiol Immunol. 2005; 292:165-200
9. Fischer Y H, Miletic H, Giroglou T, Litwak S, Stenzel W, Neumann H, von Laer D. A retroviral packaging cell line for pseudotype vectors based on glioma-infiltrating progenitor cells (2007) Journal of Gene Medicine 9:335-344
10. Fukuhara H, Martuza R L, Rabkin S D, Ito Y, Todo T. Oncolytic herpes simplex virus vector g47delta in combination with androgen ablation for the treatment of human prostate adenocarcinoma. Clin Cancer Res. 2005 Nov. 1; 11(21):7886-90
11. Garbutt M, Liebscher R, Wahl-Jensen V, Jones S, Moller P, Wagner R, Volchkov V, Klenk H D, Feldmann H, Stroher U. Properties of replication-competent vesicular stomatitis virus vectors expressing glycoproteins of filoviruses and arenaviruses. J Virol. 2004 May; 78(10): 5458-65
12. Ge J, Wen Z, Wang X, Hu S, Liu Y, Kong X, Chen H, Bu Z. Generating vesicular stomatitis virus pseudotype bearing the severe acute respiratory syndrome coronavirus spike envelope glycoprotein for rapid and safe neutralization test or cell-entry assay Ann N Y Acad Sci. 2006 October; 1081:246-8
13. Irie T, Carnero E, Okumura A, Garcia-Sastre A, Harty R N. Modifications of the PSAP region of the matrix protein lead to attenuation of vesicular stomatitis virus in vitro and in vivo. J Gen Virol. 2007 September; 88(Pt 9):2559-67
14. Hanika A, Larisch B, Steinmann E, Schwegmann-Wessels C, Herder G, Zimmer G. Use of influenza C virus glycoprotein HEF for generation of vesicular stomatitis virus pseudotypes. J Gen Virol. 2005 May; 86(Pt 5):1455-65
15. Haller O, Kochs G, Weber F. The interferon response circuit: induction and suppression by pathogenic viruses. Virology. 2006 Jan. 5; 344(1):119-30
16. Holland E C. Gliomagenesis: genetic alterations and mouse models. Nat Rev Genet. 2001 February; 2(2): 120-9
17. Janzen C, Kochs G, Haller O. A Monomeric GTPase-Negative M×A Mutant with Antiviral Activity. J Viro12000 September, 74(17):8202-8206
18. Jayakar H R, Whitt M A. Identification of two additional translation products from the matrix (M) gene that contribute to vesicular stomatitis virus cytopathology. J Virol. 2002 August; 76(16):8011-8
19. Jiang Y, Jahagirdar B N, Reinhardt R L, Schwartz R E, Keene C D, Ortiz-Gonzalez X R, Reyes M, Lenvik T, Lund T, Blackstad M, Du J, Aldrich S, Lisberg A, Low W C, Largaespada D A, Verfaillie C M. (2002) Pluripotency of mesenchymal stem cells derived from adult marrow. Nature 418:41-9
20. Kikuchi, T., Joki, T., Akasaki, Y., Abe, T, Ohno, T. (1999) Cancer Lett. 135, 47-51
21. Kleihues, P. and Cavenee, W. K. World Health Organization Classification of Tumours-Pathology and Genetics, Tumours of the Nervous system. 2000 (International Agency for Research on cancer, Lyon)
22. Loew R, Vigna E, Lindemann D, Naldini L, Bujard H. Retroviral vectors containing Tet-controlled bidirectional transcription units for simultaneous regulation of two gene activities. JMol GenMed 2006, 2(1), 107-118
23. Lun X, Senger D L, Alain T, Oprea A, Parato K, Stojdl D, Lichty B, Power A, Johnston R N, Hamilton M, Parney I, Bell J C, Forsyth P A. Effects of intravenously administered recombinant vesicular stomatitis virus (VSV(deltaM51)) on multifocal and invasive gliomas. J Natl Cancer Inst. 2006 Nov. 1; 98(21):1546-57

24. Majewski, S., Marczak, M., Szmurlo, A., Jablonska, S. & Bollag, W.; Interleukin-12 inhibits angiogenesis induced by tumor cell lines in vitro.; J. Invest. Dermatol. 1996; 106:1114-8
25. Miletic H, Bruns M, Tsiakas K, Vogt B, Rezai R, Baum C, Kuhlke K, Cosset F L, Ostertag W, Lother H, von Laer D (1999) Retroviral vectors pseudotyped with lymphocytic choriomeningitis virus. J. Virol. 73:6114-6
26. Miletic H, Fischer Y H, Neumann H, Hans V, Stenzel W, Giroglou T, Hermann M, Deckert M, Von Laer D. (2004). Selective transduction of malignant glioma by lentiviral vectors pseudotyped with lymphocytic choriomeningitis virus glycoproteins. Hum Gene Ther. 15: 1091-100
27. Miletic H, Fischer Y H, Litwak S, Giroglou T, Waerzeggers Y, Winkeler A, Li H, Himmelreich U, Lange C, Stenzel W, Deckert M, Neumann H, Jacobs A H, von Laer D. Bystander Killing of Malignant Glioma by Bone Marrow-Derived Tumor Infiltrating Progenitor Cells Expressing a Suicide Gene (2007). Molecular Therapy 15:1373-1381
28. Miletic H, Fischer Y H, Giroglou T; Rueger M A, Winkeler A, Li H, Himmelreich U, Stenzel W, Jacobs A H, von Laer D. Normal brain cells contribute to the bystander effect in suicide gene therapy of malignant glioma. (2007b) Jorurnal of Clinical Cancer Research, in press
29. Owens R J, Rose J K. Cytoplasmic domain requirement for incorporation of a foreign envelope protein into vesicular stomatitis virus. J Virol. 1993 January; 67(1): 360-5
30. Pavlovic J, Haller O, Staeheli P. Human and mouse Mx proteins inhibit different steps of the influenza virus multiplication cycle. J Virol. 1992 April; 66(4):2564-9
31. Riepl C, Mandl C. Two non-infectious flaviviruses can form an infectious alliance. Nürnberg, 2007. Poster at the annual Meeiting of the Gesellschaft für Virologie
32. Sakariassen P O, Prestegarden L, Wang J, Skaftnesmo K O, Mahesparan R, Molthoff C, Sminia P, Sundlisaeter E, Misra A, Tysnes B B, Chekenya M, Peters H, Lende G, Kalland K H, Oyan A M, Petersen K, Jonassen I, van der Kogel A, Feuerstein B G, Terzis A J, Bjerkvig R, Enger P O. Angiogenesis-independent tumor growth mediated by stem-like cancer cells. Proc Natl Acad Sci USA. 2006 Oct. 31; 103(44):16466-71
33. Shinosaki K, Ebert O, Suriawinata A, Thung S N, Woo S L. Prophylactic alpha interferon treatment increases the therapeutic index of oncolytic vesicular stomatitis virus virotherapy for advanced hepatocellular carcinoma in immune-competent rats. J Virol. 2005 November; 79(21): 13705-13
34. Shir A, Levitzki A. Gene therapy for glioblastoma: future perspective for delivery systems and molecular targets. Cell Mol Neubiol. 2001 December; 21: 645-56
35. Short M P, Choi B C, Lee J K, Malick A, Breakefield X O, Martuza R L. Gene delivery to glioma cells in rat brain by grafting of a retrovirus packaging cell line. J Neurosci Res. 1990 November; 27(3):427-39
36. Staeheli P, Pavlovic J. Inhibition of vesicular stomatitis virus mRNA synthesis by human MxA protein. J Virol. 1991 August; 65(8):4498-501
37. Sumia A, Curtin J F, Zirger J M, Xiong W, King G D, Barcia C, Liu C, Puntell M, Goverdhana S, Lowenstein P R, Castro M G. Inflammatory and Anti-glioma Effects of an Adenovirus Expressing Human Soluble Fms-like Tyrosine Kinase 3 Ligand (hsFlt3L): Treatment with hsFlt3L Inhibits Intracranial Glioma Progression. Molecular Therapy (2004) 10, 1071-1084
38. Tani H, Komoda Y, Matsuo E, Suzuki K, Hamamoto I, Yamashita T, Moriishi K, Fujiyama K, Kanto T, Hayashi N, Owsianka A, Patel A H, Whitt M A, Matsuura Y. Replication-competent recombinant vesicular stomatitis virus encoding hepatitis C virus envelope proteins. J Virol. 2007 August; 81(16):8601-12. Epub 2007 Jun. 6
39. Toda, M., Martuza, R. L., Kojima, H. & Rabkin, S. D.; In situ cancer vaccination: an IL-12 vector/replication-competent herpes simplex virus combination includes local and systemic antitumor activity, J. Immunol. 1998; 160:4457-4464
40. Trajcevski S, Solly S K, Frisen C, Trenado A, Cosset F L, Klatzmann D. Characterization of a semi-replicative gene delivery system allowing propagation of complementary defective retroviral vectors. J Gene Med. 2005 March; 7(3):276-87
41. Tyminski E, Leroy S, Terada K, Finkelstein D M, Hyatt J L, Danks M K, Potter P M, Saeki Y, Chiocca E A. Brain tumor oncolysis with replication-conditional herpes simplex virus type 1 expressing the prodrug-activating genes, CYP2B1 and secreted human intestinal carboxylesterase, in combination with cyclophosphamide and irinotecan. Cancer Res. 2005 Aug. 1; 65(15):6850-7
42. Wollmann G, Robek M D, van den Pol A N. Variable deficiencies in the interferon response enhance susceptibility to vesicular stomatitis virus oncolytic actions in glioblastoma cells but not in normal human glial cells. J Virol. 2007 February; 81(3):1479-91
43. Zimmer G, Conzelmann K K, Herrler G. Cleavage at the furin consensus sequence RAR/KR(109) and presence of the intervening peptide of the respiratory syncytial virus fusion protein are dispensable for virus replication in cell culture. J Virol. 2002 September; 76(18):9218-24

What is claimed is:

1. A tumor-specific replication-competent vector construct comprising: a vesicular stomatitis virus (VSV) vector pseudotyped with glycoprotein GP of lymphocyte choriomeningitis virus (LCMV) (VSV-LCMV-GP pseudotype vector), wherein the vector comprises a gene coding for a glycoprotein GP of LCMV and the vector either lacks a functional gene coding for envelope protein G of VSV or the envelope protein G is replaced, wherein infection of cells with the replication-competent VSV-LCMV-GP pseudotype vector causes LCMV-GP to be encoded in the genome of a progeny viral particle and subsequently expressed on the surface of the progeny viral particle; and
wherein tropism of the progeny viral particle is independent of an additional tumor-targeting element or transgene in the VSV-LCMV-GP pseudotype vector and wherein the progeny viral particle exhibits tumor-specific replication competence.

2. The VSV-LCMV-GP pseudotype vector of claim 1, wherein the envelope protein G is replaced by the glycoprotein GP of LCMV.

3. The VSV-LCMV-GP pseudotype vector of claim 1, wherein the M protein of VSV comprises mutations that reduce cytopathogenicity of VSV.

4. The VSV-LCMV-GP pseudotype vector of claim 1, wherein the vector further comprises at least one additional transgene encoding one or more of a suicide protein, an immunostimulatory protein, or a marker protein.

5. The VSV-LCMV-GP pseudotype vector of claim 4, wherein the suicide protein is the thymidine kinase of the herpes simplex virus (HSV-TK), cytosine deaminase, FKBP-FAS, or FKBP-caspase9.

6. The VSV-LCMV-GP pseudotype vector of claim 4, wherein the immunostimulatory protein is IL-2, IL-4, IL-12, neutralizing anti-TGFβ, or Flt3L.

7. The VSV-LCMV-GP pseudotype vector of claim 1, wherein the LCMV is LCMV-WE, LCMV-WE-HPI or LCMV-WE-HPIopt.

8. The VSV-LCMV-GP pseudotype vector of claim 1, wherein the progeny viral particle exhibits tumor-specific replication competence in one or more cells of a solid tumor.

9. The VSV-LCMV-GP pseudotype vector of claim 8, wherein the one or more cells are from a glioblastoma.

10. The VSV-LCMV-GP pseudotype vector of claim 1, wherein the glycoprotein GP of the VSV-LCMV-GP pseudotype vector is unmutated.

11. The VSV-LCMV-GP pseudotype vector of claim 1, wherein the tumor-specific replication competence exhibited by the progeny viral particle is independent the glycoprotein GP of the VSV-LCMV-GP pseudotype vector or any modifications thereof.

\* \* \* \* \*